United States Patent
Elyasaf et al.

(10) Patent No.: US 7,841,529 B2
(45) Date of Patent: Nov. 30, 2010

(54) MULTIPLE OPTICAL HEAD INSPECTION SYSTEM AND A METHOD FOR IMAGING AN ARTICLE

(75) Inventors: Emanuel Elyasaf, Rehovot (IL); Avishay Guetta, Rehovot (IL)

(73) Assignee: Applied Materials Israel, Ltd., Rehovot (IL)

( * ) Notice: Subject to any disclaimer, the term of this patent is extended or adjusted under 35 U.S.C. 154(b) by 910 days.

(21) Appl. No.: 10/987,083

(22) Filed: Nov. 12, 2004

(65) Prior Publication Data
US 2007/0222978 A1 Sep. 27, 2007

Related U.S. Application Data

(60) Provisional application No. 60/620,427, filed on Oct. 19, 2004.

(51) Int. Cl.
*G01N 21/88* (2006.01)

(52) U.S. Cl. .................. 235/454; 382/141; 382/149; 356/237.5; 356/236.4; 356/236.5; 356/602; 369/44.24

(58) Field of Classification Search .................. 235/454; 382/141, 149; 356/236.2, 236.4, 236.5, 602; 369/44.24
See application file for complete search history.

(56) References Cited

U.S. PATENT DOCUMENTS

| | | | |
|---|---|---|---|
| 5,351,126 A * | 9/1994 | Takada et al. ............... 356/602 |
| 5,610,895 A * | 3/1997 | Izumi et al. ............... 369/44.24 |
| 5,699,477 A | 12/1997 | McCree |
| 6,208,411 B1 | 3/2001 | Vaez-Iravani |
| 6,248,988 B1 | 6/2001 | Krantz |
| 6,366,690 B1 * | 4/2002 | Smilansky et al. .......... 382/149 |
| 6,578,961 B2 | 6/2003 | Vaez-Iravani |
| 6,639,201 B2 | 10/2003 | Almogy |
| 6,671,042 B1 | 12/2003 | Almogy |
| 2004/0095572 A1 * | 5/2004 | Iwa et al. .................. 356/237.2 |
| 2005/0018554 A1 * | 1/2005 | Shiba ....................... 369/44.24 |
| 2006/0007531 A1 * | 1/2006 | Korengut et al. ............ 359/362 |
| 2007/0019856 A1 * | 1/2007 | Furman et al. .............. 382/141 |
| 2008/0002556 A1 * | 1/2008 | Lee et al. ................ 369/112.27 |

\* cited by examiner

*Primary Examiner*—Allyson N Trail
(74) *Attorney, Agent, or Firm*—SNR Denton US LLP

(57) ABSTRACT

A method for imaging an article, the method includes: (i) providing short duration light pulses; (ii) directing the light pulses, by multiple optical heads, to illuminate multiple spaced apart areas of an article; and (iii) directing light from the multiple areas towards multiple two-dimensional light sensors; whereas (iv) imparting motion between the article and the multiple optical heads during the stages of providing and directing. An apparatus for inspecting an article that includes: (i) at least one pulsating source for providing short duration light pulses; (ii) multiple optical heads, adapted to direct the light pulses to illuminate multiple spaced apart areas of an article and to collect light from the multiple areas towards multiple two-dimensional light sensors; and (iii) a positioning device which is adapted to impart motion between the article and the multiple optical heads.

17 Claims, 5 Drawing Sheets

MULTIPLE OPTICAL HEAD INSPECTION SYSTEM AND A METHOD FOR IMAGING AN ARTICLE

CROSS REFERENCE TO RELATED APPLICATIONS

This application claims the benefit of U.S. Provisional Patent Application 60/620,427, filed Oct. 19, 2004, titled: Multi Modes Inspection System, which is incorporated herein by reference.

BACKGROUND OF THE INVENTION

1. Field of the Invention

The present invention relates to a system and method for inspecting articles such as wafers, reticles and the like.

2. Description of the Related Art

The inspection of semiconductor wafers is typically performed by scanning a laser beam across a wafer's surface and collecting light scattered therefrom. The scanning operation is conducted by scanning the laser beam across the wafer surface in a first direction using one of a variety of known deflectors, such as acousto-optic deflectors or electromechanical deflectors, while moving a stage that supports the wafer thereon in a second direction that is typically orthogonal to the first direction.

Another type of inspection includes illuminating an area and acquiring an image. U.S. Pat. No. 5,699,477 of Alumot el al provides an example of such inspection systems.

There are various devices and methods for scanning a laser beam, such as acousto-optic devices, electromechanical deflectors, and the like. There is a greater emphasis on the throughput of inspection device and accordingly on the throughput of scanners, as the design rules for semiconductors rapidly shrink without a corresponding decrease of the inspection sequence time period or the overall size of semiconductor dies or wafers.

High throughput inspection systems utilize optical beam arrays as well as electron beam arrays for increasing throughput. Hybrid systems that include electron beam illumination, electro-optical conversion and light beam detection are also known. Electron beams also provide higher resolution. U.S. Pat. No. 6,671,042 of Almogy, U.S. Pat. No. 6,639,201 of Almogy et al., U.S. Pat. Nos. 6,578,961 and 6,208,411 of Vaez-Iravani and U.S. Pat. No. 6,248,988 of Krantz, which are incorporated herein by reference, describe state of the art inspection systems.

Some prior art inspection systems utilize relatively large objective lenses and additional optical components in order to capture a large field of view (FOV). The complexity and cost of lenses as well as their development period increases in a non-linear manner as their respective size grows.

Various image processing methods are known in the art. They include die-to-die comparison, cell-to-cell comparison and die to database comparison.

There is a need to provide an efficient system and method for high throughput inspection.

SUMMARY OF THE INVENTION

An apparatus for inspecting an article, the apparatus includes: (i) at least one pulsating source for providing short duration light pulses; (ii) multiple optical heads, adapted to direct the light pulses to illuminate multiple spaced apart areas of an article and to collect light from the multiple areas towards multiple two-dimensional light sensors; and (iii) a positioning device, such as but not limited to a stage, which is adapted to impart motion between the article and the multiple optical heads.

Conveniently, each optical head includes an optical component for blocking light of at least one frequency.

A method for imaging an article, the method includes: (i) providing short duration light pulses; (ii) directing the light pulses, by multiple optical heads, to illuminate multiple spaced apart areas of an article; and (iii) directing light from the multiple areas towards multiple two-dimensional light sensors; whereas the method further comprises (iv) imparting motion between the article and the multiple optical heads during the stages of providing and directing.

Other features of the present invention will become apparent from the following detailed description considered in connection with the accompanying drawings that disclose embodiments of the present invention.

BRIEF DESCRIPTION OF THE DRAWINGS

The foregoing and other objects, features, and advantages of the present invention will become more apparent from the following detailed description when taken in conjunction with the accompanying drawings. In the drawings, similar reference characters denote similar elements throughout the different views, in which.

DETAILED DESCRIPTION OF THE PREFERRED EMBODIMENTS

Reference will now be made in greater detail to exemplary embodiments of the present invention. In the following description made in conjunction with the exemplary embodiments of the present invention, a variety of specific elements are described. The following detailed description is of exemplary embodiments of the invention but the invention is not limited thereto, as modifications and supplemental structures may be added, as would be apparent to those skilled in the art. Also, in the following description of the present invention, a detailed description of known functions and configurations incorporated herein is omitted.

In particular, but without limitation, while an exemplary embodiment may be disclosed with regard to the inspection of a specimen surface by detecting reflected light using a light source and a detecting unit that are disposed on a common side of a specimen (a "reflective system"), it would be readily apparent to one skilled in the art that the teachings are readily adaptable to the inspection of a specimen by detecting transmitted light with a detecting unit that is on a side of a specimen opposite to that of the light source (a "transmissive system"). While the reflective system and the transmissive system differ, for one example by the absence of a beam splitter in the transmissive system, the principles of the present invention are applicable to both types of systems. As would be understood by one skilled in the art, both types of systems may be utilized separately or together in an inspection of a specimen.

The invention provides a system that includes multiple optical heads, whereas the multiple optical heads can simultaneously image multiple areas of the inspected wafer. Each optical head includes its own collection path. At least a portion of the illumination path can be shared by multiple optical heads. For example, each optical head can include its own light source but this is not necessarily so. According to an embodiment of the invention light pulses generated by a single light source can be provided to multiple optical heads by illumination optics such as mirrors and beam splitters.

Figure 1:
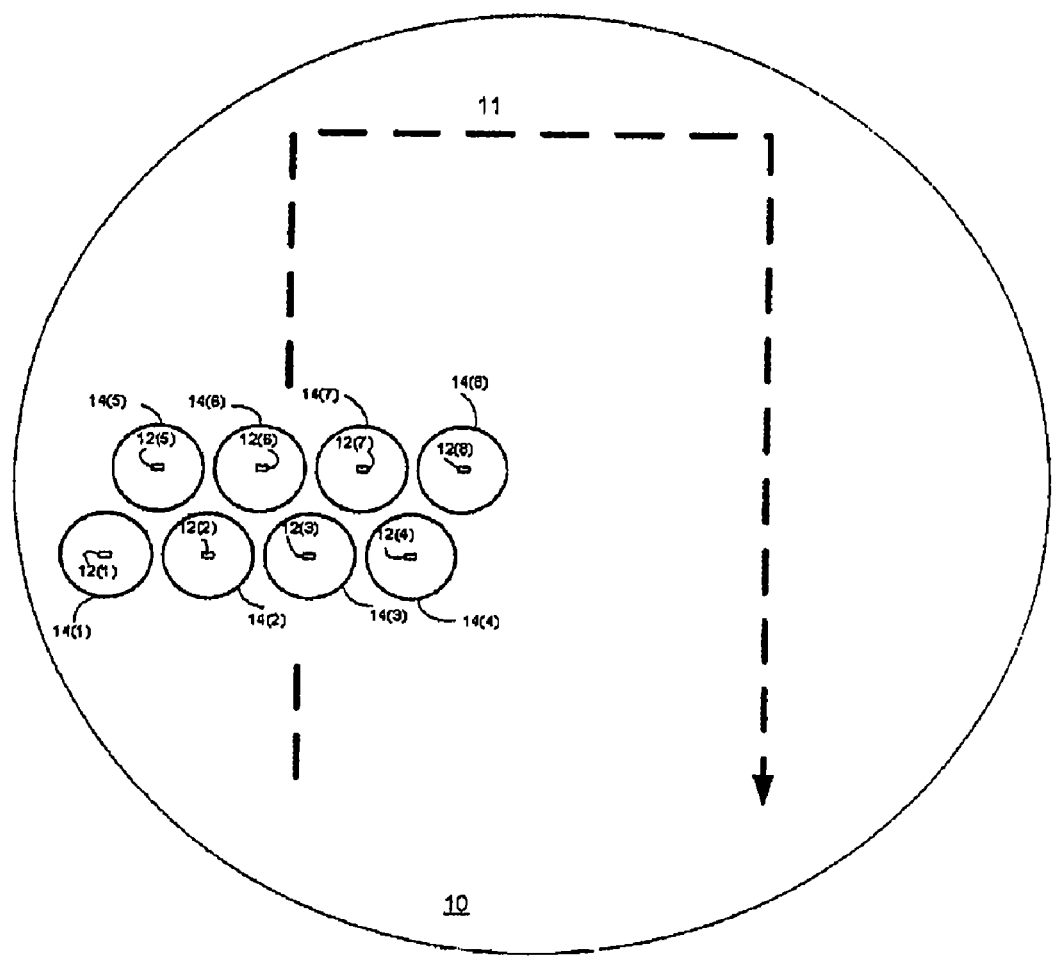
FIG. 1 illustrates the coverage, relative spacing and field of view (FOV) of multiple optical heads, according to an embodiment of the invention.

FIG. 1 illustrates the coverage, relative spacing and field of view (FOV) of multiple optical heads, according to a first embodiment of the invention.

The system includes eight optical heads. Each optical head includes an objective lens that has a certain field of view. FIG. 1 illustrates a wafer 10, eight objective lens diameters 12(1)-12(8) of eight optical heads, and the field of view 14(1)-14(8) of each of said objective lenses.

The eight optical heads are arranged in two columns, each of four optical heads. Conveniently, and as illustrated by FIG. 1, the columns of objective lens are offset in relation to each other, thus these columns scan different area of the wafer once a relative movement is introduced between the optical heads and the wafer 10.

The movement introduced between wafer 10 and the multiple optical heads (also referred to scanning path) is designed such as to cover a predefined portion of wafer 10 or even the whole wafer. This movement is usually defined in response to the size and shape of the inspected area and in response to the spatial relationship between the different coverage areas.

In order to cover the entire wafer 10, the optical heads may follow a serpentine path, such as path 11, but this is not necessarily so and they can follow different paths.

According to an embodiment of the invention each optical head can operate in multiple wavelengths, such as visible and ultra violet wavelengths.

Figure 2:
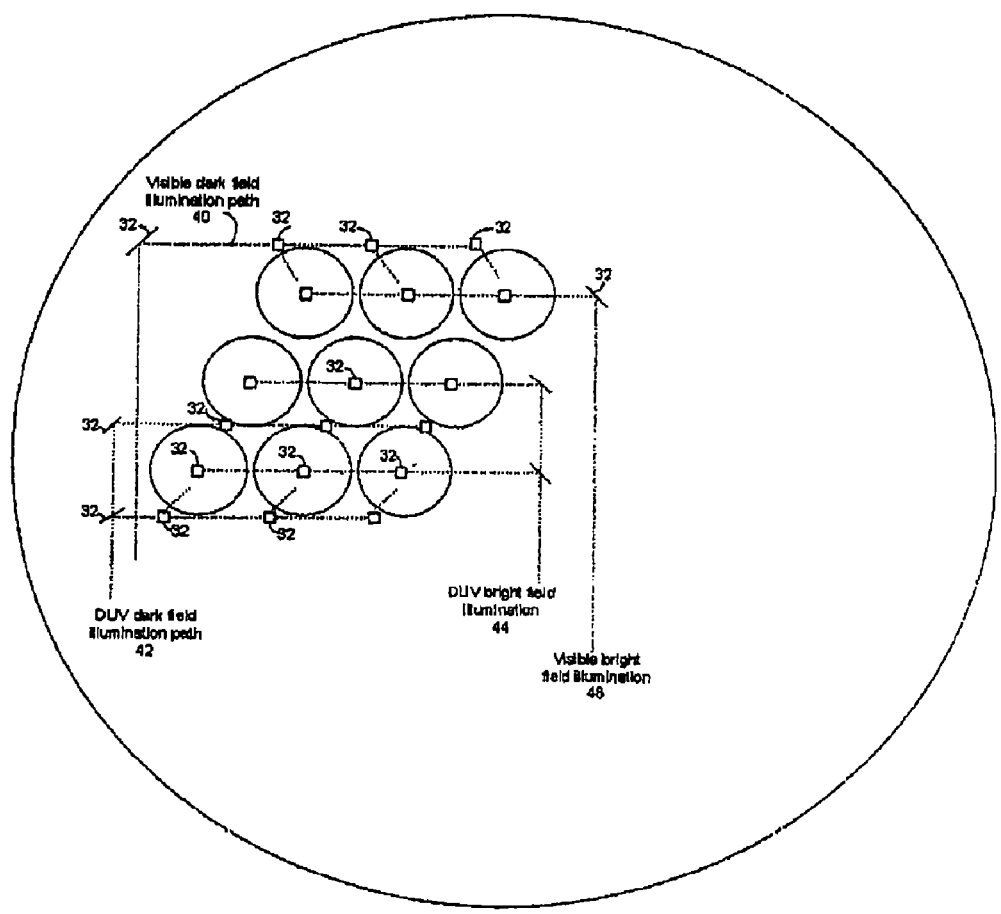
FIG. 2 illustrates the coverage, relative spacing and field of view (FOV) of multiple optical heads, according to another embodiment of the invention.

FIG. 2 illustrates the coverage, relative spacing and field of view (FOV) of multiple optical heads, as well as various illumination paths, according to another embodiment of the invention. According to this embodiment the system includes nine optical heads. Each optical head includes an objective lens that has a certain field of view. The different optical heads are arranged at three columns of three optical head each.

According to an embodiment of the invention, each optical head can be adapted to operate at a single wavelength. Conveniently, some of the optical heads operate at the deep ultraviolet range while some optical heads operate at the visible range. Conveniently, the number of optical heads that operate at shorter wavelengths is larger than the number of optical heads that operate at a longer wavelength. The inventors used two rows of three optical heads each that operate at the deep ultraviolet range and a single column that operates at the visible range.

According to an embodiment of the invention the amount of optical heads is inversely proportional to their fields of view. Thus, the wavelength as well as the numerical aperture of the optical heads can determine the amount of optical heads that operate at a certain wavelength.

FIG. 2 illustrates four illumination paths, all illustrated by dashed lines—visible light dark field illumination path 40, deep ultraviolet dark field illumination path 42, visible light bright field illumination path 46 and deep ultraviolet bright field illumination path 44. These paths can start by two or more light sources, whereas one or more light sources provide visible light and one or more light sources can provide deep ultraviolet light. For example, the visible bright field and dark field illumination paths can receive visible light from the same light source, but this is not necessarily so. Many ways for distributing light are known in the art, and FIG. 2 illustrates a light distribution system that includes beam splitters and mirrors, both denoted 32.

Figure 3:
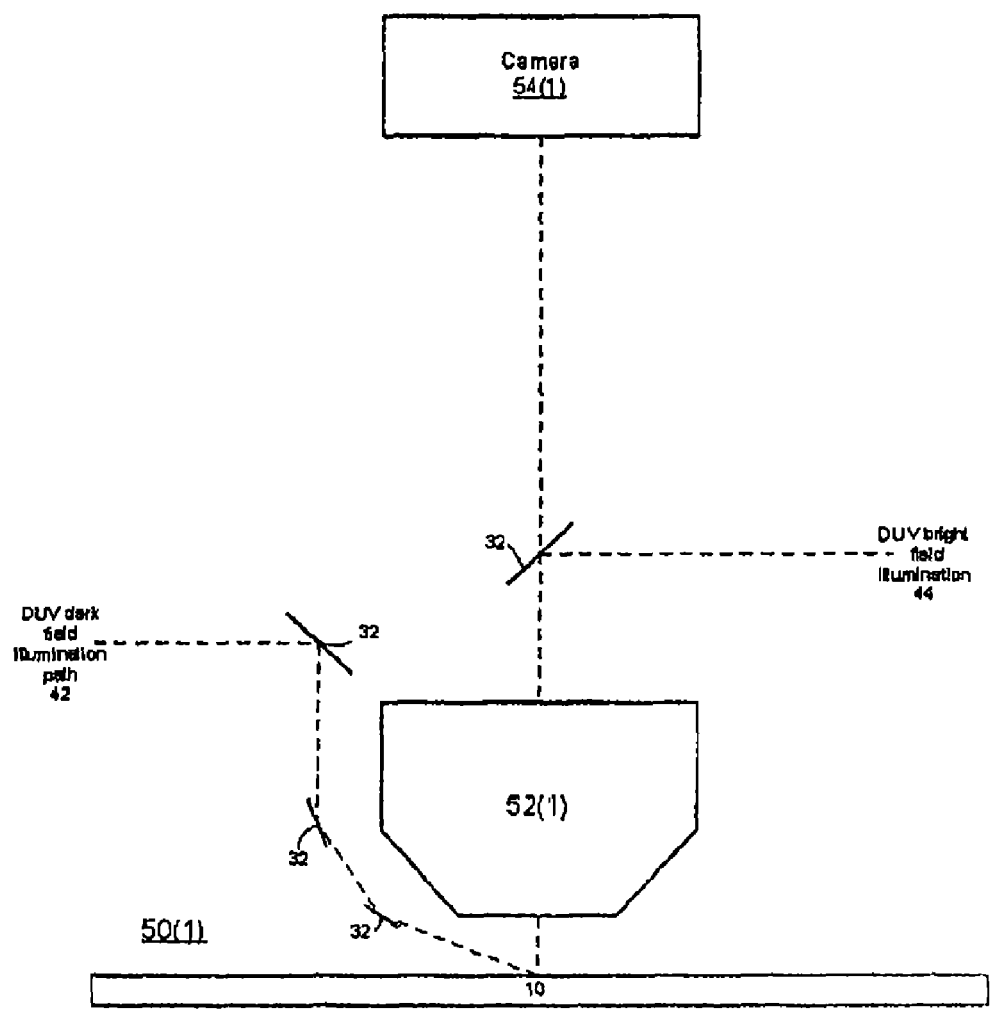
FIG. 3 illustrates a single camera optical head, according to an embodiment of the invention.

FIG. 3 illustrates a single-camera optical head 50(1), according to an embodiment of the invention.

Optical head 50(1) includes an objective lens 52(1), multiple mirrors and beam splitters 32 as well as a single camera unit 54(1). The multiple beam splitters and mirrors 32 direct deep ultraviolet light at a dark filed path or at a bright field path.

Typically, the optical head 50(1) may include additional components such as auto focus components and the like. According to an embodiment of the invention, the optical heads are rigidly connected to each other. In such a case, reading from one or more auto-focus components can assist in determining the required height of the multiple optical heads. According to another embodiment, each optical head can be lifted or lowered independently. Thus, each head can have its own auto-focus circuitry. According to another embodiment of the invention, the optical heads are arranged in groups and each group can be lifted or lowered such as to be positioned at a required height.

The inventors used a system that is characterized by the following characteristics: visible light of 532 nm and deep ultraviolet light of 266 nm. The system generates pixels (at 266 nm) of 60-150 nm and an objective lens diameter of 35 nm. Conveniently, the camera includes a light intensifier followed by a CMOS sensor array of at least 1000×1000 pixels. It is noted that these are only exemplary numbers and that a system according to the invention can be characterized by different characteristics.

Figure 4:
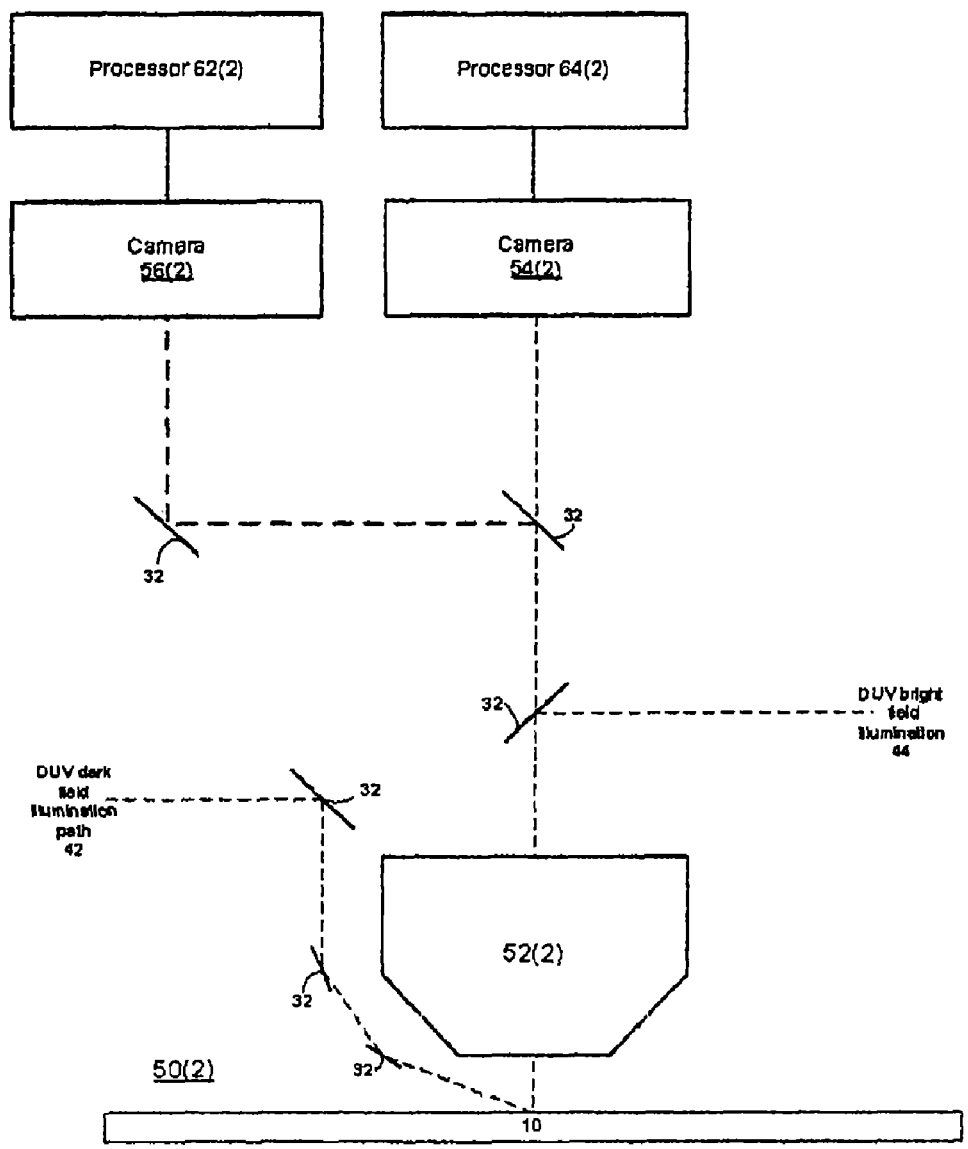
FIG. 4 illustrates a dual camera optical head, according to an embodiment of the invention.

FIG. 4 illustrates a dual camera optical head 50(2), according to an embodiment of the invention. The optical head 50(2) includes two camera units 54(2) and 56(2) instead of the single camera unit of optical head 50(1). Optical head 50(2) also includes an additional mirror and beam splitter for directing light to both camera units.

Typically, optical head 50(1) as well as optical head 50(2) include additional optical components such as spatial filters, relay lenses and the like, but for simplicity of explanation they are omitted from FIGS. 3 and 4.

According to an embodiment of the invention the two cameras can be focused to imaginary points of different planes. For example, the first camera unit 54(2) can be focused onto a imaginary plane located just above the upper surface of wafer 10 while the second camera unit 56(2) can be focused onto a imaginary plane located below the upper surface of wafer 10.

Each camera can be connected to a separate processor, such as processors 62(2) and 64(2) that are connected to camera units 54(2) and 56(2), respectively.

This is not necessarily so, as more than a single camera can be connected to a single processor that in turn can use multi-camera techniques for processing the images acquired by the different cameras. Various prior art methods for multi-perspective processing are known in the art and can be applied by the processors.

The system typically includes a controller for coordinating the operation of various components of the system. For example, the short duration light pulses should be generated when the optical heads are positioned in certain locations; the optical heads can be configured (for example by selectively filtering received light of certain wavelength) during the imaging process.

According to another embodiment of the invention a multiple camera optical head can simultaneously receive light of two wavelengths and send a light of a first wavelength to a first camera while sending light of a second wavelength to a second camera. This can be achieved by using wavelength selective components such as but not limited to filters.

Conveniently, a processor of the system is adapted to detect defects by processing detection signals acquired from different locations of a substantially repetitive pattern.

Figure 5:
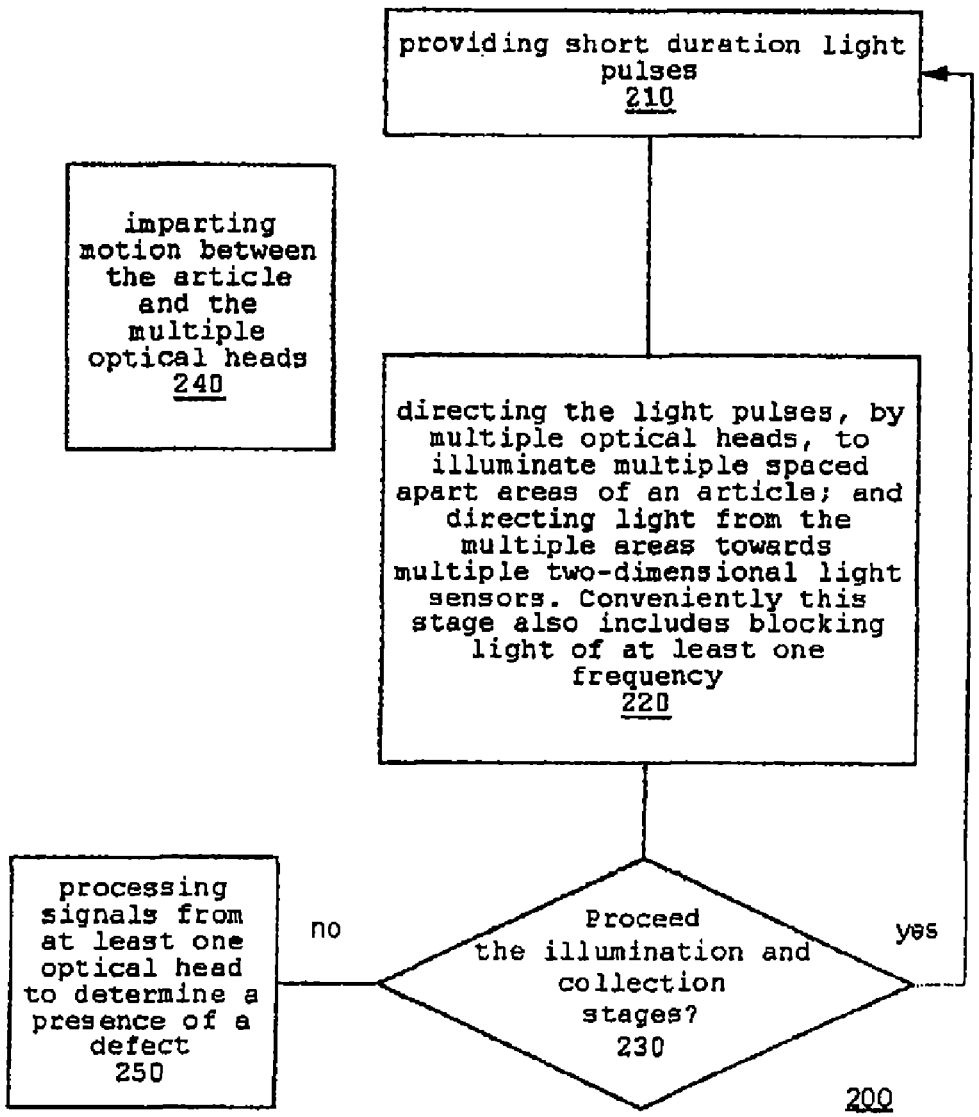
FIG. 5 illustrates a method for imaging an article, according to an embodiment of the invention.

FIG. 5 illustrates a method 200 for imaging an article, according to an embodiment of the invention.

Method 200 starts by stage 210 of providing short duration light pulses. According to an embodiment of the invention the short duration light pulses are of at least one wavelength.

Stage 210 is followed by stage 220 of directing the light pulses, by multiple optical heads, to illuminate multiple spaced apart areas of an article; and directing light from the multiple areas towards multiple two-dimensional light sensors. Conveniently this stage also includes blocking light of at least one frequency.

Stage 210 and 220 are repeated multiple times, until a certain scanning path is completed. Said repetition is illustrated by stage 230 in which the method determines whether to proceed (the scanning path did not end) by jumping to stage 210 or to end the imaging process and conveniently start a processing stage.

Method 200 also includes stage 240 of imparting motion between the article and the multiple optical heads. Conveniently, this stage includes introducing a movement along a scan axis that is oriented in relation to an imaginary axis between two adjacent optical heads.

Method 200 usually includes a stage 250 of processing signals from at least one optical head to determine a presence of a defect. Stage 250 can be executed at least partially in parallel to stages 210-230, but this is not necessarily so. According to various embodiments of the invention the processed signals are acquired from different dies, thus the processing is a die to die method. According to another embodiment of the invention the processed signals are acquired from different location of a substantially repetitive pattern, thus the processing is a cell to cell processing method.

Conveniently, the short duration light pulses undergo speckle reduction prior reaching the optical heads.

According to various embodiments of the invention each camera unit includes one or more cameras. Multiple cameras within a single camera unit can be used, for example, to increase throughput each camera unit may include multiple cameras, each receiving light from a different area of the illuminated wafer. The areas may slightly overlap, but this is not necessarily so. A multiple camera configuration is known in the art and needs no additional details.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

What is claimed is:

1. An apparatus for inspecting an article, comprising:
    at least one pulsating source for providing short duration light pulses through at least one illumination path, a portion of the light pulses having a first characteristic and another portion of the light pulses having a second characteristic, the first characteristic different than the second characteristic;
    a first group of optical heads adapted to receive light pulses of the first characteristic;
    a second group of optical heads adapted to receive light pulses of the second characteristic, wherein the first and second group of optical heads are further adapted to direct the light pulses having the first and second characteristics to illuminate multiple spaced apart areas of the article and to direct light from the multiple areas towards multiple two-dimensional light sensors; and
    a positioning device adapted to impart motion between the article and the first and second groups of optical heads.

2. The apparatus of claim 1 wherein at least one optical head comprises an objective lens for collecting light from a single area.

3. The apparatus of claim 1 wherein at least one optical head defines two collection paths, a first path for light of a first frequency and a second path for light of a second frequency.

4. The apparatus of claim 3 wherein the first frequency is within an ultraviolet through extreme ultra violet frequency range.

5. The apparatus of claim 3 wherein the first frequency is within a visible frequency range.

6. The apparatus of claim 1 wherein the positioning device introduces a movement along a scan axis oriented in relation to an imaginary axis between two adjacent spaced apart optical heads.

7. The apparatus of claim 1 wherein a distance between adjacent illuminated areas is much larger than a dimension of an illuminated area.

8. The apparatus of claim 1 further comprising a processor, coupled to the two-dimensional light sensors, for detecting a defect.

9. The apparatus of claim 8 wherein the processor is adapted to detect defects by processing detection signals acquired from different dies.

10. The apparatus of claim 8 wherein the processor is adapted to detect defects by processing detection signals acquired from different locations of a substantially repetitive pattern.

11. The apparatus of claim 1 further comprising speckle reduction means.

12. A method for imaging an article, the method comprising:
    providing short duration light pulses over at least one illumination path, a portion of the light pulses having a first characteristic and another portion of the light pulses having a second characteristic, the first characteristic different than the second characteristic;
    receiving by a first group of optical heads light pulses of the first characteristic;

receiving by a second group of optical heads light pulses of the second characteristic, wherein the first and second group of optical heads are further adapted to direct the light pulses having the first and second characteristics to illuminate multiple spaced apart areas of the article and direct light from the multiple areas towards multiple two-dimensional light sensors; and imparting motion between the article and the first and second groups of optical heads.

13. The method of claim 12 wherein the step of imparting motion comprises introducing a movement along a scan axis oriented in relation to an imaginary axis between two adjacent optical heads.

14. The method of claim 12 further comprising processing signals from at least one optical head to determine a presence of a defect.

15. The method of claim 14 wherein the signals are acquired from different dies.

16. The method of claim 14 wherein the signals are acquired from different locations of a substantially repetitive pattern.

17. The method of claim 12 further comprising speckle reduction.

* * * * *